United States Patent [19]

Cleary et al.

[11] Patent Number: 5,746,738
[45] Date of Patent: May 5, 1998

[54] LASER SURGICAL DEVICE

[75] Inventors: David J. Cleary, Alexandria, Va.; Hyung S. Ryu, Washington, D.C.

[73] Assignee: Cleary & Oxford Associates, Alexandria, Va.

[21] Appl. No.: 751,428

[22] Filed: Nov. 20, 1996

[51] Int. Cl.$^6$ ............................................ A61B 17/36
[52] U.S. Cl. ........................................ 606/15; 606/17
[58] Field of Search .................... 606/14, 15, 16, 606/17, 9

[56] References Cited

U.S. PATENT DOCUMENTS

| | | |
|---|---|---|
| 4,780,898 | 10/1988 | Sundqvist . |
| 4,834,093 | 5/1989 | Littleford et al. ............... 606/16 X |
| 4,913,142 | 4/1990 | Kittrell et al. ....................... 606/7 |
| 5,041,109 | 8/1991 | Abela ............................ 606/15 |
| 5,116,344 | 5/1992 | Sundqvist . |
| 5,125,922 | 6/1992 | Dwyer et al. . |
| 5,150,704 | 9/1992 | Tatebayashi et al. . |
| 5,163,936 | 11/1992 | Black et al. . |
| 5,219,347 | 6/1993 | Negus et al. . |
| 5,281,211 | 1/1994 | Parel et al. . |
| 5,290,274 | 3/1994 | Levy et al. . |
| 5,290,280 | 3/1994 | Daikuzono ....................... 606/16 |
| 5,298,026 | 3/1994 | Chang ............................. 606/15 |
| 5,312,396 | 5/1994 | Feld et al. . |
| 5,451,221 | 9/1995 | Cho et al. . |
| 5,454,782 | 10/1995 | Perkins ........................ 606/16 X |

*Primary Examiner*—Jennifer Bahr
*Assistant Examiner*—Sonya Harris-Ogugua
*Attorney, Agent, or Firm*—Nixon & Vanderhye P.C.

[57] ABSTRACT

In a surgical catheter or probe, an array of multiple surgical laser beams are directed such that several laser beams intersect at a precise point on, or in, the body of a surgical patient. The power density of the laser energy of the intersecting beams at the point of intersection is sufficient to alter or ablate the patient's tissue, bone or fluid. The energy of the individual laser beams before or after the point of intersection is not sufficient to injure the body of the patient. The apparatus may be embodied as a catheter or probe for an endoscope, or can be used in a separate mechanism such that the laser beams enter the surgical patient at different locations but intersect at a point within the patient.

23 Claims, 6 Drawing Sheets

5,746,738

LASER SURGICAL DEVICE

FIELD OF THE INVENTION

The invention relates broadly to the field of laser medical devices, and more particularly, to laser surgical devices.

BACKGROUND OF THE INVENTION

Lasers have been used in the medical field to destroy unwanted tissue by directing a laser beam with an appropriate wave length onto the surgical site, often through an endoscopic device. The laser procedures require careful control of several parameters, such as the power level of the laser, the length of the laser pulse, the frequency of the pulse, and the overall duration of the procedure. Procedures and devices using lasers have been developed to destroy tissue inside a body cavity, such as inside an artery, by passing laser light through an optical fiber onto the unwanted tissue, thereby ablating the unwanted tissue.

The use of lasers has many advantages, but it also has limitations. Conventionally, lasers are invasive in that a cut is required into the body to provide an open path from the laser beam source to the laser site target. Cutting and surgery in addition to that needed to make a lasing path is often necessary because lasers are sometimes difficult to direct to the surgical site. Optical fibers can be used to transmit the laser beams of certain wavelengths to the site, but optical fibers are damaged by some lasers at high energy levels. Laser radiation can unintentionally damage tissue, such as arterial walls or tissue surrounding the surgical site.

While most prior medical applications of laser involve a single laser beam, multiple beam laser systems have been employed for certain applications. Other patents have described the use of multiple lasers, but none of the devices described in those patents can focus multiple lasers onto a specific site. U.S. Pat. No. 4,408,602 discloses a system having two beams, but they are not used simultaneously. U.S. Pat. Nos. 4,931,053 and 4,951,663 disclose two lasers producing beams aligned onto a common output, but does not describe a multiple beam apparatus. U.S. Pat. No. 4,925,523 discloses apparatus using two beams of lasers at wave lengths of 195 mm and 308 mm. U.S. Pat. No. 5,125,922 discloses a laser which switches back and forth between two wave lengths. U.S. Pat. Nos. 5,163,936 and 5,219,347 disclose two beams, an aiming beam and a surgical beam, variations of which are described in several other patents. U.S. Pat. No. 5,290,274 discloses directing two types of beams to a single site, but the beams are directed parallel along the same axis and do not intersect at only one site. U.S. Pat. No. 5,312,396 discloses the coupling of two beams, but they are successive in orientation as opposed to simultaneous. Elekta Instrument AB of Stockholm, Sweden, has several devices and patents using multiple beams of radiation, but those devices apply to gamma ray devices and are not applicable for use in a catheter or optical fiber.

In view of the deficiencies associated with existing medical lasers, a long-felt need exists for the development of a surgical laser system such as this invention.

SUMMARY OF THE INVENTION

A novel and unobvious laser focusing apparatus has been developed that allows for a plurality of laser beams to intersect at a single focal point in or on a patient. Collectively, the beams have enough energy to ablate tissue at the focal point. However, each individual laser beam will not by itself damage tissue. The use of several relatively low-powered lasers that ablate tissue only when collectively directed to a single target has inherent safety features. For example, a single laser would likely have to be at a higher energy level than the optical fibers used in the invention could transmit without being damaged to achieve the same effect as does the plurality of beams. Moreover, any potential damage to surgical sites in the vicinity of the laser site target is reduced because each of the several laser beams by itself does not damage tissue.

When used in an endoscopic catheter, the focusing mechanism will increase the fluence (energy/area) at the focal point without unduly affecting the diameter of any single optical fiber. Greater precision can be achieved with a small diameter focus and higher overall power density, which is achieved through the increased number of small radius laser beams of this invention.

In an endoscopic catheter, the instantaneous power in the optical fiber at any given time should be below the threshold that would damage the fiber by self-focusing or surface breakdown. Self-focus damage limits peak power that could be transmitted through the optical fiber, and surface breakdown restricts the pulse energy profile. By transmitting the energy through several optical fibers, each with a fraction of the total energy, this invention minimizes the potential of damaging the optical fibers.

With certain lasers, such as the He:Ne laser, human body tissue will transmit the radiation for several millimeters through the tissue. At low wattage, laser radiation will transmit through tissue with no effect on the tissue itself. Therefore, a laser beam can be transmitted through a vessel wall (such as a blood vessel which is only a few millimeters thick) without cutting the vessel wall and with no adverse effects on the tissue wall.

In the preferred embodiment, the catheter shall be large enough to include several optical fibers which each transmit a laser beam. At the output, i.e., the distal end, of the catheter, the lasers shall be directed at a common point (the confluence) forward of the distal end of the catheter. The confluence of the beams from the catheter shall be enough to produce a fluence sufficient to ablate tissue at the point where the laser beams intersect. With the appropriate laser at sufficiently low power, the single laser beams can be transmitted through several millimeters of tissue. Only where the beams intersect, will there be enough power to ablate tissue.

By selecting the appropriate laser wave length, wattage, pulse rate, the distance from each laser source to the point of intersection, and the number of lasers, the effect on body tissue can be carefully and precisely controlled. The invention may utilize a variety of types of lasers, e.g., He:Ne, Nd:YAG, Er:YAG and others. The power level, the pulse duration, the frequency of the pulses, and the distance from the tip of the laser optical fiber to the point where the laser beams converge, can be varied. For instance, an embodiment of this invention employs ten separate optical fibers, each carrying Nd:YAG laser beams at a fundamental wave length of 106 μ. Each of the lasers operates at an energy level, pulse duration, and separation between pulses (e.g., greater than 200 ns) that does not damage the optical fiber, but with sufficient power such that at the point of convergence of the six lasers, the fluence will ablate tissue. For tissue that might require 900 mJ/mm$^2$ for ablation, ten lasers at a power level of 100 mJ/mm$^2$ could be utilized.

By directing the movement of more than one laser to an identified site and providing sufficient energy at the point of intersection of the beams to surgically alter and/or ablate human tissue, bone or fluid, the system improves the techniques of laser surgery in a manner heretofore not contemplated. The focusing mechanism also allows for the interchanging of lasing systems to change the radiation pattern (wave length, frequency and intensity) without the need to change the output end or output optics of the catheter or probe of the laser device.

The number of lasers incorporated in a catheter is limited only by the size of the catheters and fiber optic laser conduits. The more lasers per catheter, the less power each will have to transmit.

It is an object of the present invention to improve upon the treatments that can be performed with laser radiation and increase the variety of treatments which can be performed safely and effectively through the use of laser radiation.

DETAILED DESCRIPTION OF THE DRAWINGS

Figure 1:
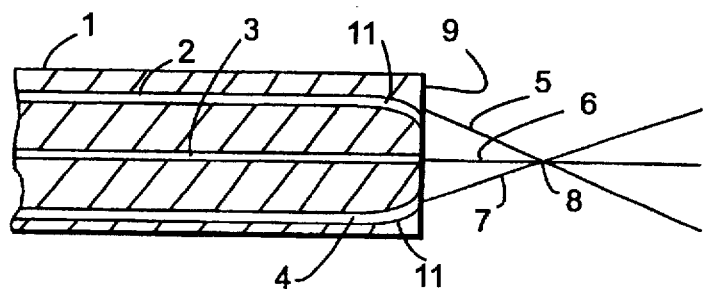
FIG. 1 is a simplified longitudinal cross-sectional view of a catheter housing three optical fiber lasers.

The apparatus illustrated in FIG. 1 includes a laser catheter 1, inside of which are a plurality of lumens 2, 3, 4, e.g., optical fibers, through which laser beams 5, 6, 7 are directed. The laser beams 2 and 4, by virtue of the lumens through which the optical fibers are directed (catheters can be molded such that fiber lumens can be curved within the catheter), to intersect at point 8 distal of the end of the catheter. At the point of intersection the beams also intersect the axial laser beam 6 passing through center lumen 3. Laser beams 2 and 4 are directed toward the center line between them such that those beams always intersect at the centerline. By changing the angles that laser beams 2 and 4 form with respect to axial laser beam 3, the distance from the end of the catheter to the intersection 8 of the beams can be manipulated as desired. The angle at which the beams are projected from the distal end 9 of the catheter 1 may be fixed or adjustable.

Figure 2:
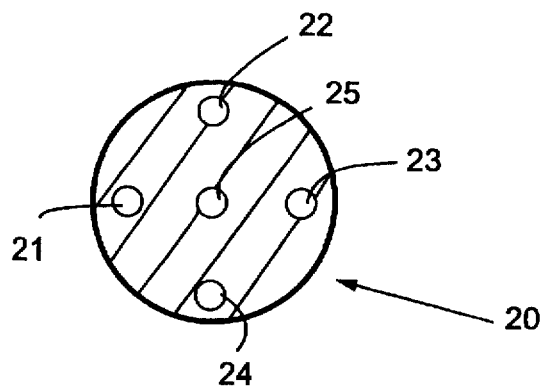
FIG. 2 is a simplified transverse cross-sectional view with five laser lumens.

FIG. 2 shows an end view of a laser catheter 20 similar to catheter 1, but with five laser beams. Beams 21, 22, 23, 24 are all controlled by the curvature of the lumen (11 in FIG. 1) adjacent the distal end of the catheter 20 such that the angle formed between those beams 21, 22, 23, 24 and the center beam 25 are all equal, resulting in the beams all intersecting at the same point.

Figure 3:
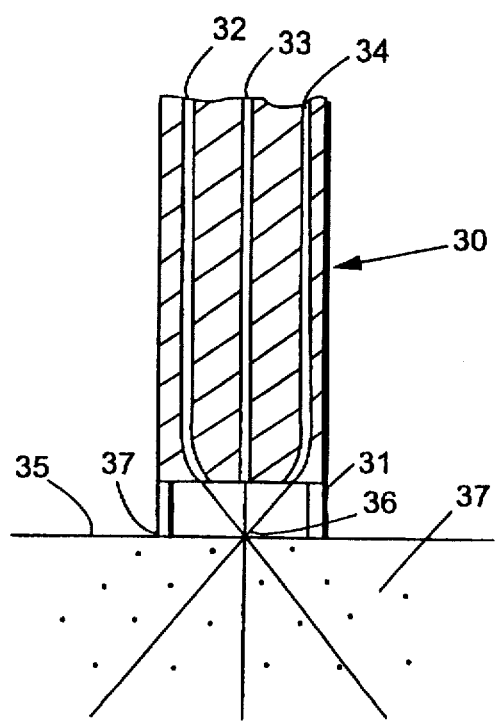
FIG. 3 shows a longitudinal cross-section of a laser probe/catheter having a depth intersection device to position the point of intersection of the laser beams onto skin.

FIG. 3 shows a laser catheter 30 with a collar 31 around the end to keep laser beam conduits 32, 33, 34, a controlled distance away from the surface 35, e.g., skin, to be treated by the lasers. In this configuration, the device would be useful for a number of dermatological procedures that require removing surface tissue from the skin, without undesirable penetration beneath the skin. After the beams intersect at point 36, they can penetrate the tissue 37 without sufficient power to damage that tissue. The point of intersection 36 may be in the plane of the distal end 37 of the collar 31 or may be beyond that plane.

Figure 4:
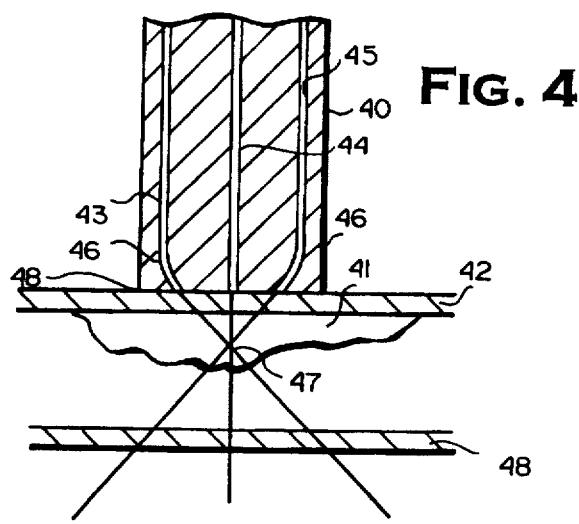
FIG. 4 shows a longitudinal cross-section of a laser device emitting lasers that penetrate the walls of a blood vessel to ablate material on the inside of the wall.

FIG. 4 shows an external probe 40 being used to ablate material 41 on the inside wall 42 of a vessel, e.g., a blood vessel. The probe has at least three laser beam pathways or optical fiber lumens 43, 44, 45. The axial laser pathway 44 is straight, but the off axis pathways 43, 45 include bends 46 that direct their respective beams to a point 47 of intersection beyond the distal end 48 of the probe. Because the laser beams do not intersect until they penetrate the vessel wall 42, the vessel wall is not damaged. At the point of intersection, the beams have sufficient power to ablate material 41, such as plaque on the interior wall of an artery, but the beams individually will not have sufficient power to damage any other tissue, such as the opposite wall 48 of the vessel. This configuration of the device can also be used to ablate unwanted tissue under the surface of the skin.

Figure 5:
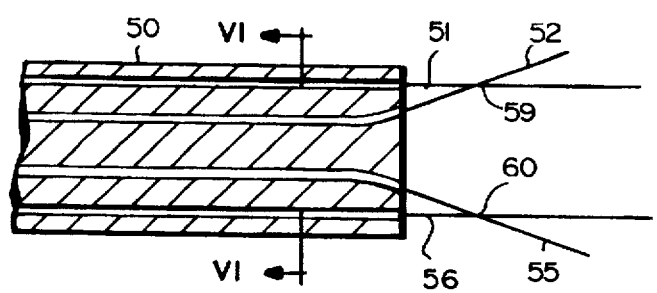
FIG. 5 is a longitudinal cross-sectional view of a laser catheter having four pairs of laser lumens.

FIG. 5 shows an endoscopic catheter 50 having multiple lumens, e.g., optical fibers, for laser beams 51 to 58. These beams form four points of intersecting laser beams. The laser beams 51 and 56 near the perimeter of a catheter 50 are directed straight ahead beyond the distal end of the catheter, and laser beams 52 and 55 near the axial center of the catheter are directed outward such that laser beam 51 intersects beam 52 at point 59 and beam 55 intersects beam 56 at point 60. At the points of intersection, the accumulative energy of the beam pairs will be greater than the individual beams, and sufficient to ablate unwanted tissue of plaque build-up.

Figure 6:
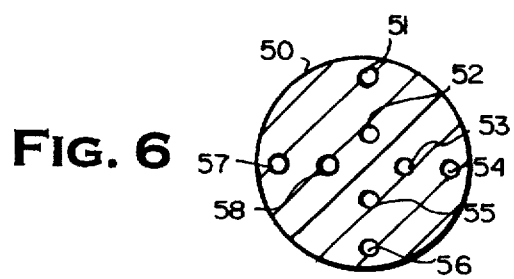
FIG. 6 shows a cross-sectional end view along line IV—IV of the device shown in FIG. 5.

FIG. 6 shows a cross section of the endoscopic laser catheter 50 shown in FIG. 5. Laser beams for beams 51, 54, 56 and 57 near the periphery of the catheter are directed straight by their respective lumens. Laser beams 52, 53, 55 and 58 are angled away from the axis of the catheter by their respective lumens, so that those beams intersect respective ones of the straight beams emanating from the lumens near the periphery of the catheter.

Figure 7:
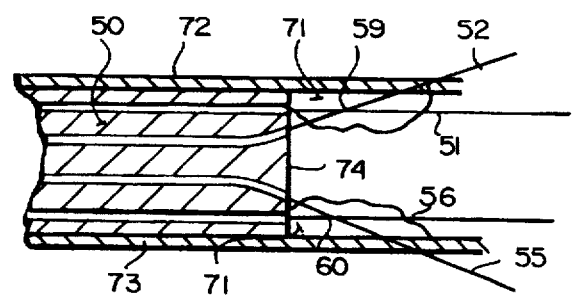
FIG. 7 shows a longitudinal cross section of another embodiment, of a laser catheter inserted in a blood vessel to ablate material on the inner walls of the blood vessel.

FIG. 7 illustrates the endoscopic catheter 50 shown in FIGS. 5 and 6, being used to ablate unwanted tissue 71 on the inside of a blood vessel wall 72, 73. Laser beam 51, directed straight ahead from the distal end 74 of the catheter, intersects beam 52 at point 59, where the combined laser energy can ablate unwanted material along the inside of the vessel wall.

Figure 8:
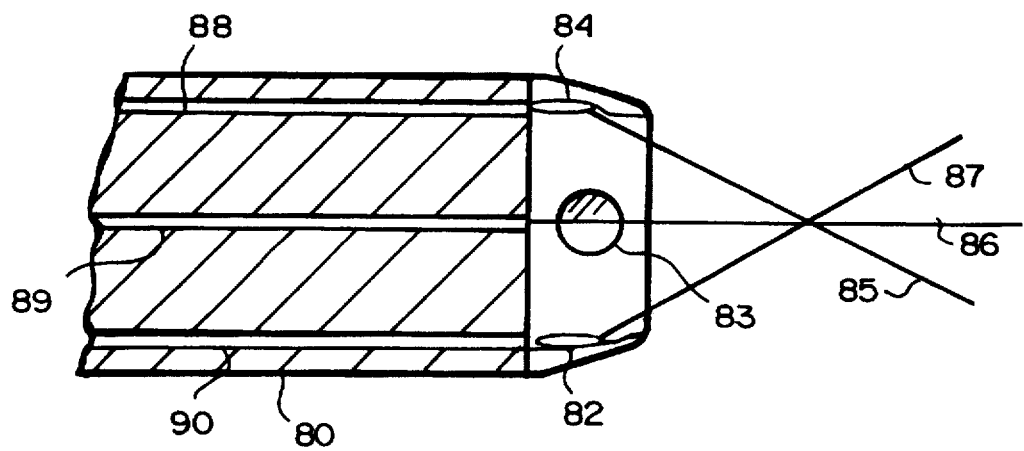
FIG. 8 shows a longitudinal cross-section of another embodiment of a catheter having multiple laser beams focused toward the axial line of the catheter by mirrors.
Figure 9:
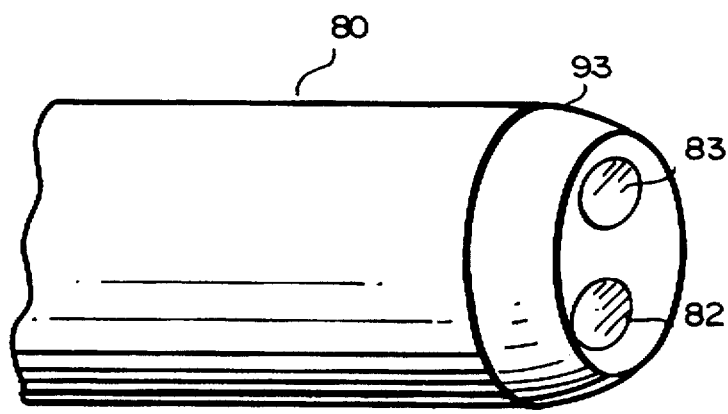
FIG. 9 is a perspective view of the catheter shown in FIG. 8.

FIG. 8 shows a laser probe 80, which may be implemented as an external probe or an endoscopic catheter. The probe 80 uses mirrors 82, 83, 84 (and others symmetrically positioned but not shown) to direct laser beams 85, 86, 87 (and perhaps other beams not shown), from straight line lumens, e.g., optical fibers, 88, 89, 90, to an external point of intersection 91. Laser beams 85 and 87 are directed by lumens 88, 90 toward mirrors 82 and 84, where they are reflected toward the focal point 91, at which point they intersect laser beam 86 coming from the center lumen 89 of the probe 80. The mirrors 82, 83, 84 are concave, to cause the laser beams to converge, increasing the fluence of the beams at the surgical site where the beams intersect. FIG. 9 shows a perspective view of probe 80, and details of an arrangement of the mirrors 82, 83 within the tip 93 of the probe.

Figure 10:
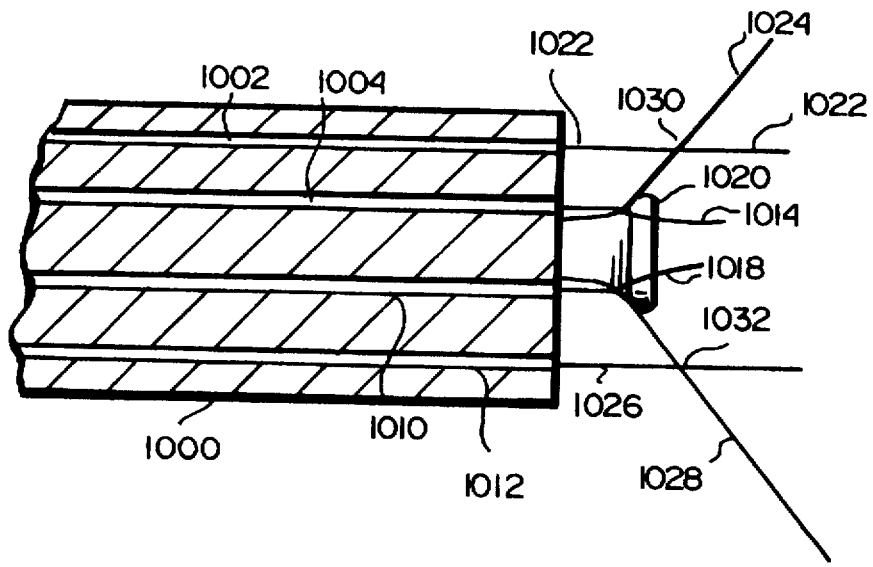
FIG. 10 shows a longitudinal cross section of another catheter having laser beams focused toward the perimeter of the catheter by of mirrors.
Figure 11:
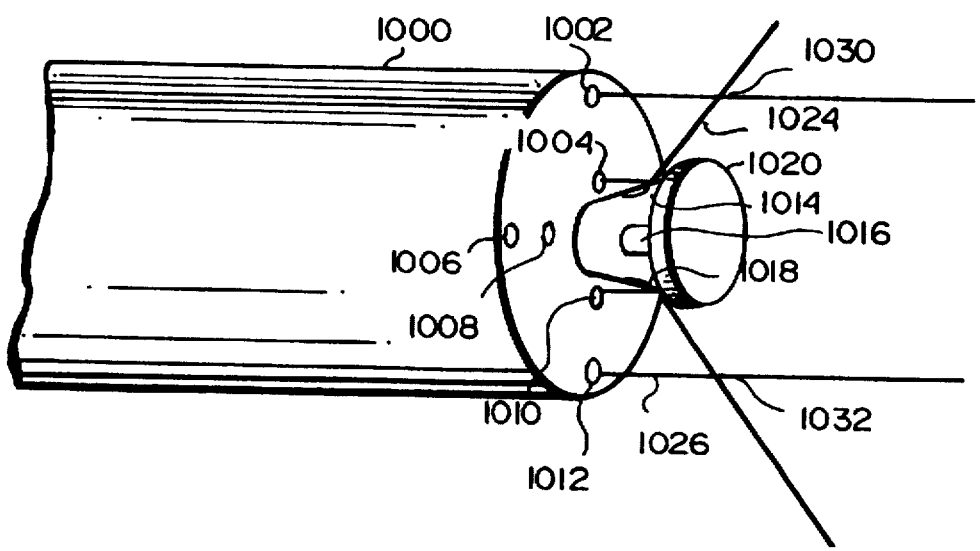
FIG. 11 is a perspective view of the catheter shown in FIG. 10.

FIGS. 10 and 11 show a probe/catheter 1000 having four pairs of straight line lumens (shown as 1002, 1004, 1006, 1008, 1010, 1012) that reflect off four mirrors (one hidden from view) 1014, 1016, 1018 on a mirror post 1026. The laser beams 1022, 1026 (one beam hidden and one not shown) pass through lumens 1002 and 1012 (and another beam passes through lumen 1006) around the periphery of the probe catheter are directed straight and do not reflect off mirrors. Beams 1024, 1028 (and two not shown) pass through lumens 1004, 1008, 1010 (one hidden) emanating from an interior ring of optical fiber lumens nearer to the center of the probe. These beams are reflected outward by a ring of concave mirrors 1014, 1016, 1018 (one not shown) such that the beams from the outer ring lumens (1002, 1006, 1012) intersect with the beams from their paired inner ring lumen 1004, 1008, 1010 at focal points 1030, 1032 (and two intersection points not shown). At the points of intersection the accumulated energy levels of the combined beams are sufficient to ablate material at the intersection points, but the individual beams do not have sufficient energy as they travel either before or beyond the points of intersection to damage tissue.

Figure 12:
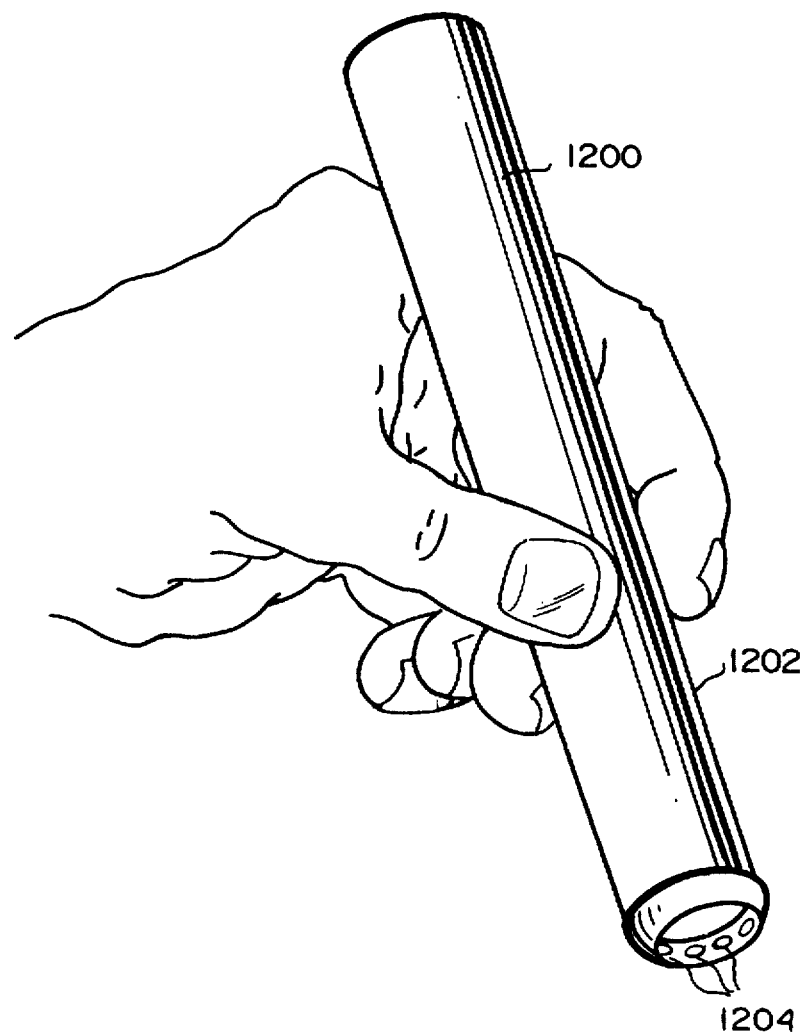
FIG. 12 shows another catheter focusing several laser beams onto a target with mirrors, and which catheter is being used externally on a surgical patient.

FIG. 12 shows a probe/catheter 1200 that is a larger version of the probe/catheter 80 illustrated in FIGS. 8 and 9. In this configuration of the probe/catheter 1200, the laser beams are not contained within a catheter, but rather are enclosed in a fixed probe tube container 1202 such that the laser beams can be directed either manually, or according to an input from imaging and marking systems commonly used in medicine. The laser beams are conveyed through optical fiber lumens in the tube container and reflected by mirrors 1204 to a point of intersection.

Figure 13:
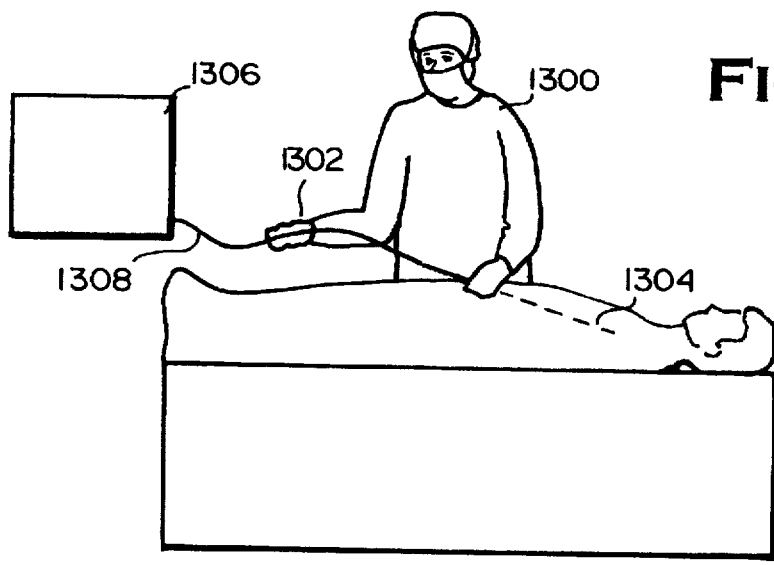
FIG. 13 shows a laser generator, a patient, and a surgeon holding an example of an internal endoscopic catheter with multiple laser beam paths, that is inserted inside the patient. Within the catheter are optical fibers that conduct the laser beams to a point inside a patient.

FIG. 13 shows a surgeon 1300 holding an endoscopic catheter 1302, inside of which are optical fibers that transmit laser beams to a common intersection point(s) within the patient's body 1304. The catheter 1302 is inserted into the patient 1304, where the beams intersect at the point(s) where tissue is to be ablated. The laser beams are generated by a laser generator 1306 and conveyed by fibers 1308 to the catheter 1302.

Figure 14:
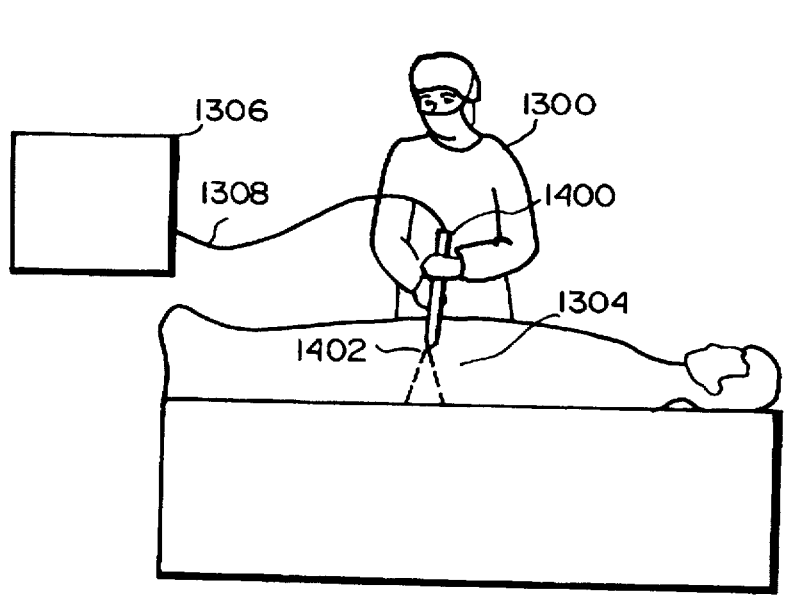
FIG. 14 shows a laser generator, a patient, and a surgeon holding an example of an external multiple laser beam probe in which the laser beams are directed from outside the patient to a point within the patient.

FIG. 14 shows a surgeon 1300 holding an external probe 1400, which transmits multiple laser beams generated by the laser generator 1306. The beams are transmitted inside the patient 1304 through body tissue, without surgically cutting the tissue. At the point where the beams intersect 1402 tissue is ablated inside the body.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A laser beam delivery system for removing human or animal tissue from a surgical site by simultaneously irradiating the tissue with a plurality of laser beams that intersect at the surgical site to ablate tissue, said system comprising:

a conduit having a plurality of optical fibers for transmitting laser beams, wherein the fibers extend through said conduit to a distal end of the conduit place near the surgical site, and said laser beams are directed by the distal end of the conduit to the point of intersection at the surgical site, and wherein each of the laser beams individually has insufficient energy level to ablate the tissue, and wherein the laser beams at the point of intersection have a combined energy level sufficient to ablate the tissue at the surgical site.

2. The laser system of claim 1 further comprising a section in a first fiber of said optical fibers proximate to the distal end of the conduit, and angled with respect to an axis of the conduit to direct a laser beam through the first fiber to the point of intersection with another laser beam passing through a second fiber of said optical fibers.

3. The laser system of claim 1 wherein the point of intersection is offset from and along an axis of the conduit and is beyond the distal end of the conduit, and the second fiber directs a second laser beam in a straight line from the distal end of the conduit to the point of intersection.

4. The laser system of claim 1 wherein the conduit is an endoscopic catheter.

5. The laser system of claim 1 wherein the conduit is an external surgical probe for directing the point of intersection onto skin, and wherein the distal end of the probe is placed adjacent the skin and near the surgical site.

6. The laser system of claim 5 further comprising a collar extending from the distal end of the probe to a plane perpendicular to the axis of the conduit and including the point of intersection.

7. A laser catheter as in claim 1 wherein said laser beam is a He:Ne laser.

8. A multiple laser catheter comprising:

a plurality of optical fiber pairs extending through said catheter for directing laser beams out from a distal end of the catheter to a point of intersection of the laser beams where the combined energy of the beams is sufficient to ablate tissue, and wherein each of the beams has an individual energy insufficient to ablate tissue;

a first fiber in each of said fiber pairs having a first output at the distal end for directing a first laser beam in a first direction parallel to an axis of the catheter;

a second fiber in each of said fiber pairs having a second output at the distal end for directing a second laser beam in a second direction forming an acute angle with the first direction.

9. A laser catheter as in claim 8 wherein said optical fiber pairs are four pairs arranged symmetrically about the axis of the catheter, and each of said pairs direct a pair of laser beams to a point of intersection.

10. A surgical laser catheter comprising an endoscopic catheter having a plurality of lumens for directing a plurality of laser beams to one or more points of beam intersection beyond a distal end of the catheter wherein each of the laser beams individually has insufficient energy levels to ablate tissue and wherein the laser beams at the point of intersection have the combined energy level sufficient to ablate tissue.

11. A laser catheter as in claim 10 wherein said plurality of lumens comprise at least two pair of lumens arranged symmetrically about an axis of the catheter.

12. A method as in claim 11 wherein step (b) further comprises transmitting the beams through body tissue without harming the tissue, except at the point of intersection.

13. A laser catheter as in claim 10 wherein said laser beam is a He:Ne laser.

14. A surgical laser catheter system comprising:

an endoscopic catheter having optical fibers for transmitting laser beams beyond a distal end of the catheter to a point of intersection at which at least two of the beams intersect to ablate tissue, wherein the laser beams individually have an energy level insufficient to ablate tissue, and the intersecting laser beams have a combined energy level sufficient to ablate tissue at the point of intersection; and said distal end of the catheter having laser reflectors arranged to direct one or more of the beams from the fibers to the point of intersection.

15. A method for ablating tissue in a body with a laser catheter or probe comprising the steps of:

a. positioning the catheter or probe proximate the tissue to be ablated;

b. transmitting a plurality of laser beams through the catheter or probe;

c. directing at least one pair of the laser beams to a point of intersection distal to the catheter or probe and in the tissue to be ablated, wherein each of the laser beams individually has an energy level insufficient to ablate tissue; and d. ablating tissue at the point of intersection by combing the individual energy levels from the laser beams to focus sufficient energy to ablate tissue.

16. A laser beam delivery system for removing tissue from a surgical site by irradiating the tissue with multiple laser beams simultaneously, said system comprising:

a catheter for directing the beams to the surgical site through optical fibers extending through the catheter and said fibers positioned near a periphery of the catheter;

said beams individually each have an energy level insufficient to ablate tissue;

at least one of the optical fibers being slightly bent at an angle to direct a laser beam transmitted through the fiber toward a center line of the catheter where the laser beams intersect at a point where the laser beams in combination have a sufficient energy level to ablate tissue at the point.

17. The laser system of claim 16, further including a center optical fiber extending along a center axis of the catheter, with a center laser beam being transmitted through the center optical fiber to the point of the intersection of laser beams transmitted through the optical fibers near the periphery of the catheter.

18. The laser system of claim 16 further including mirrors to direct the beams, such that beams being transmitted from optical fibers near the periphery of the catheter are reflected to the point of intersection.

19. The laser system of claim 16 where the conduit is applied to skin outside the body, and laser beams from the conduit enter the body at different locations and the beams intersect at a point inside the body where surgical ablation occurs.

20. A laser beam delivery system for removing tissue from a surgical site by irradiating the tissue with multiple laser beams, where each beam has energy level insufficient to ablate tissue, said system comprising:

a catheter having optical fibers for transmitting the laser beams toward the surgical site;

said optical fibers including a plurality of outer fibers near the periphery of the catheter and said outer fibers direct laser beams straight from an exit of the catheter, and a plurality of inner optical fibers arranged concentrically inside a circumference formed by the optical fibers near the periphery of the catheter, said inner optical fibers being angled to direct laser beams to intersect with beams from the optical fibers near the periphery of the catheter at the surgical site, and at each point of intersection the combined energy of the beams is sufficient to ablate tissue.

21. The laser system of claim 20 further including mirrors mounted at the end of the catheter to direct the beams, such that beams being transmitted from optical fibers near the center of the catheter are reflected by mirrors to intersect with laser beams transmitted from the optical fibers near the periphery of the catheter.

22. A skin treatment system comprising a probe having a distal end adapted to be applied to a section of skin of a patient, said probe having optical fibers to transmit laser beams beyond the distal end of the probe to a point of intersection where at least two of the beams combine to ablate tissue below the skin, and wherein the laser beams individually have an energy level insufficient to ablate skin or tissue, and the laser beams have a combined energy level at the point of intersection sufficient to ablate tissue.

23. A laser surgical system comprising a catheter having a distal end adapted to be positioned in a patient near tissue to be ablated, said catheter having optical fibers to transmit laser beams beyond the distal end of the catheter to a point of intersection where at least two of the beams combine to ablate tissue below the skin, and wherein the laser beams individually have an energy level insufficient to ablate tissue, and the laser beams have a combined energy level at the point of intersection sufficient to ablate the tissue.

* * * * *